United States Patent [19]

Mano et al.

[11] Patent Number: 5,506,241
[45] Date of Patent: Apr. 9, 1996

[54] ARGATROBAN PREPARATIONS FOR OPHTHALMIC USE

[75] Inventors: Tomiya Mano, Ibaraki; Jin Shiomura, Funabashi, both of Japan

[73] Assignee: Mitsubishi Chemical Corporation, Tokyo, Japan

[21] Appl. No.: 313,556

[22] Filed: Sep. 27, 1994

Related U.S. Application Data

[63] Continuation-in-part of Ser. No. 32,264, Mar. 17, 1993, abandoned.

[30] Foreign Application Priority Data

Mar. 18, 1992 [JP] Japan ..................... 4-061947

[51] Int. Cl.$^6$ .................................. A61K 31/445
[52] U.S. Cl. ............................. 514/317; 514/912
[58] Field of Search ........................ 514/317, 912

[56] References Cited

U.S. PATENT DOCUMENTS

| 4,117,127 | 9/1978 | Okamoto et al. | 424/247 |
| 4,131,673 | 12/1978 | Okamoto et al. | 424/247 |
| 4,201,863 | 5/1980 | Okamoto et al. | 526/166 |
| 5,141,947 | 8/1992 | Tamao et al. | 514/314 |

FOREIGN PATENT DOCUMENTS 61-48829  10/1986  Japan.

OTHER PUBLICATIONS

Hijikata—Okunomiya et al. Thromb. Res. vol. 45 No. 5, 1987, pp. 699–702.
Schneider, Thromb. Res. vol. 64 No. 6, 1991, pp. 677–689.
Jaffe et al., Opthalmology vol. 97 No. 2, 1990, pp. 184–189.

*Primary Examiner*—Zohreh Fay
*Attorney, Agent, or Firm*—Wenderoth, Lind & Ponack

[57] ABSTRACT

A method for preventing fibrin formation in anterior chamber characterized by administering argatroban into the anterior chamber is provided. A phermaceutical preparation for irrigation, eye drop, and drip infusion to effect the said method is also provided.

18 Claims, 3 Drawing Sheets

ARGATROBAN PREPARATIONS FOR OPHTHALMIC USE

This application is a continuation-in-part of now abandoned application Ser. No. 08/032,264, filed Mar. 17, 1993 now abandoned.

INDUSTRIAL FIELD OF INVENTION

This invention relates to a novel use of argatroban in the field of ophthalmology. More specifically, it relates to the novel use of argatroban for inhibiting fibrin formation in the anterior chamber.

BACKGROUND OF THE INVENTION

Argatroban is a generic name assigned to (2R, 4R)-4-methyl-1-[$N^2$-((RS)-3-methyl-1,2,3,4-tetrahydro- 8-quinolinesulfonyl)-L-arginyl]-2-piperidinecarboxylic acid hydrate represented by the formula:

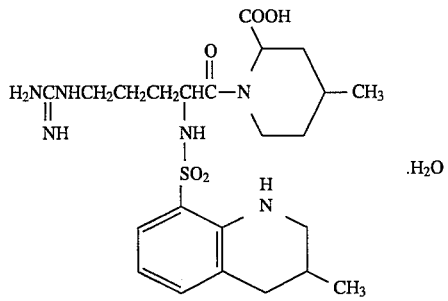

This compound belongs to $N^2$-arylsulfonyl-L-arginineamides.

As is disclosed in Japanese Patent Application 88786/1979, argatroban is a selective anti-thrombin substance having entirely new action mechanism which has never been observed in hitherto known medicines. The action mechanism of argatroban includes the selective inhibition of thrombin caused by steric binding of the tripod structure of argatroban to the active site of thrombin. Argatroban strongly inhibits three major actions of thrombin, i.e., (1) fibrin formation, (2) stabilization of fibrin by activation of Factor VIII, and (3) platelet aggregation. As a result, argatroban is clinically known to be applicable in treating limbs ulcer in chronic arterial obstruction and pain at rest, and improving frigidity.

The present inventors completed this invention as explained hereunder in detail by searching for applications of argatroban other than in chronic arterial obstruction in the light of the above unique action mechanism of argatroban.

After intraocular surgery such as retinal and vitreous surgery, cataract operation, and glaucoma operation, post operative fibrin formation in the anterior chamber is often observed. This is a very important problem since the fibrin formation must be prevented for establishing satisfactory post operative management. For example, the fibrin formation after intraocular lens implantation results in not only poor visual prognosis, but also possible development of serious condition, such as complication of glaucoma. The fibrin formation after vitreous surgery also interferes with the post operative fundus examination to disturb the appropriate treatment or management of vitreo-retinal disease. Further, the fibrin formation can cause intractable anterior proliferative vitreo-retinal condition.

On the background as explained above, it has been recognized that prevention of postoperative fibrin formation is very important, but is measure to cope with it has been reported to date.

EXPLANATION OF THIS INVENTION

Figure 1:
FIG. 1: Fibrin formation in the anterior chamber by the laser irradiation under condition A. This is a photograph replacing a figure showing the appearance of the animal.

Argatroban has been hitherto administered for preventing the formation of the blood clot in blood vessels, i.e., thrombus.

The present inventors conducted a pharmacological experiment to see whether or not argatroban can show its unique in vivo activity in tissues or organs other than blood. It was found that argatroban can prevent the fibrin formation after intraocular surgery. The present invention is based on this finding. No report has been presented to confirm such activity of argatroban in vivo other than in blood. Argatroban has not yet been applied in the ophthalmic area.

In order to prevent the post-opertive fibrin formation in the eye, Argatroban can be administered, for example, by direct application to the anterior chamber, by application as an eye drop, by intravenous application, or by application in an intraocular irrigating solution, and the like methods. The intravenous application is preferably by drip infusion. Further, argatroban can be injected under the retina. Argatroban can be administered prior to, during, or after the operation.

The pharmaceutical formulation used for administering argatroban is a parenteral solution such as intraocular irrigating solution, eye drop, or drip infusion.

The intraocular irrigating solution of this invention is prepared by dissolving argatroban in, for example, sterile and purified water. In this case, if necessary, pharmaceutically acceptable additives can be added such as a buffering agent and an isotonic agent for adjusting the composition of the solution to that of the aqueous humor. Specifically, glucose, sodium chloride, potassium chloride, calcium chloride, magnesium sulfate, sodium hydrogen carbonate, etc., can be added.

The eye drop of this invention is an aqueous ophthalmic solution, non-aqueous ophthalmic solution, ophthalmic suspension, or opthalmic emulsion. The eye drop of this invention is prepared by dissolving or suspending argatroban in sterile purified water, physiological saline, etc., as the aqueous solvent, or cotton seed oil, soybean oil, sesame oil, peanut oil, and the like plant oil as the non-aqueous solvent. In this case, isotonic agent, pH adjusting agent, viscousifying agent, suspending agent, emulsifying agent, preserving agent, and the like pharmaceutically acceptable additives can be added, if necessary. Specifically, the isotonic agents include sodium chloride, boric acid, sodium nirate, potassium nitrate, D-mannitol, glucose, etc. Specific examples of the pH adjusting agents include boric acid, anhydrous sodium sulfite, hydrochloric acid, ciric acid, sodium citrate, acetic acid, potassium acetate, sodium carbonate, borax, etc. Specific examples of the viscosifying agents include methylcellulose, hydroxypropylmethylcellulose, polyvinyl alcohol, sodium condroitin sulfate, polyvinylpyrrolidone, etc. Specific examples of the suspending agents include polysolvate 80, polyoxyethylene hydrogenated caster oil 60, polyoxy hydrogenated caster oil, etc. Specific examples of the emulsifying agents include yolk lecithin, polysolvate 80, etc. Specific examples of the preserving agents include benzalkonium chloride, benzethonium chloride, chlorobutanol, phenylethyl alcohol, paraoxybenzoic acid esters, etc.

The drip infusion of this invention is an aqueous solution for injection and a suspension for injection. The drip infusion of this invention is prepared by dissolving argatroban in distilled water for injection, physiological saline, Ringer solution, or in these solvents containing a small amount of water-soluble organic solvent such as ethanol, glycerine which are used as a solvent. In this case, isotonic agent, pH adjusting agent, emulsifying agent, preserving agent, and the like pharmaceutically acceptable additives can be added, if necessary. Specific examples of the isotonic agents include sodium chloride, glucose, D-sorbitol, D-mannitol, etc. The pH adjusting agents include anhydrous sodium sulfite, hydrochloric acid, citric acid, sodium citrate, etc. The emulsifying agents include yolk lecithin, polysolvate 80, etc. The preserving agents include benzalkoniumchloride, benzethonium chloride, paraoxybenzoate esters, etc.

As is illustrated in the following examples, the administration of argatroban to the anterior chamber together with self-plasma causes inhibition of fibrin formation. Such result shows that the fibrin formation may be inhibited by delivery of argatroban into the anterior chamber. This result shows that argatroban can be given by direct administration to the anterior chamber and, similarly, it is understood that the fibrin formation after intraocular operation can be inhibited by adding it into ocular infusion. The experiments on rabbits conducted by the present inventors to date showed that the argatroban concentration in the anterior chamber 1 hour after the intravenous administration of 10 microgram/kg/min, 40 microgram/kg/min, and 400 microgram/kg/min argatroban are 5.7±0.7, 41.0±4.2, and 881± 110 mg/ml, respectively. Further, administration of eye drops of 2 mg/ml argatroban in saline results in the concentration of 23.7±19.1 mg/ml in the anterior chamber. This means that by intravenous and eye-drop administrations argatroban is delivered into the anterior chamber and the fibrin formation in the organ can be inhibited.

The optimal dose of argatroban for man may vary depending on the administration route, administration time, age of the patient, condition of patients, etc. Generally, applicable may be 1 to 50 mg/kg/day for intravenous administration, an ocular solution of 1 to 6 mg/ml argatroban for eye drop administration, and 0.1 microgram/ml to 0.6 mg/ml argatroban in intraocular irrigation solution.

More specifically, a 0.05–0.5% solution of argatroban for the eye drop is administered at 1 or 2 drops per dosage in 1–6 dosages per day. An ointment containing 0.05–0.5% argatroban is applied to eye at a suitable amount 1–6 times per day. An ocular irrigation containing 0.001–0.5% argatroban is irrigated during operations. In the case of an intravenous drip infusion, argatroban is applied at 30–300 mg/24 h.

Usually, argatroban is administered during operations in the form of ocular irrigation, while for post-operations in the form of eye drop, drip infusion and ointment.

Argatroban can be administered to patients who are suspected to have fibrin formation caused by destruction of blood anterior chamber barrier (BAB). For example, such patients include those who are treated by intraocular surgery such as cataract operation, ablatio retinae operation, vitreous operation, glaucoma operation, keratoplasty. Further, patients who can receive argatroban are those suffering from intrinsic uveitis, and receiving laser therapy.

Anti-inflammatory agents which can be administered together with argatroban are exemplified by steroids such as dexamethasone, sodium dexamethasone sulfobenzoate, sodium betamethasone phosphate, sodium dexamethasone phosphate and fluorometholone, and non-steroids such as aspirin, indomethacin, pranoprofen (niflan), and diclofenac sodium (voltaren).

Steroids may be administered as shown below. A 0.01–0.2% solution of steroids for the eye drop is administered at a ratio of 1 or 2 drops per dosage and 1–6 dosages per day. An ointment containing 0.01–0.2% steroids is applied to the eye at a suitable amount 1–6 times per day. An ocular irrigation containing 0.001–0.2% steroids is irrigated during operations. In the case of an intravenous drip infusion, steroids are applied at 1–10 mg of the active ingredient/24 h.

Aspirin is administered orally at a ratio of 0.5–1.5 g per dosage and in total 1–4.5 g per day, while a suppository containing 0.1–1.5 g of aspirin is divided into 1–3 portions and administered 1–3 times per day. Indomethacin is administered orally at 25 mg per dosage and 1–3 times per day, while a suppository containing 25–50 mg of indomethacin is administered 1–2 times per day. Pranoprofen (niflan) is administered orally at 75 mg per dosage and 3 times per day, while an eye drop containing 0.1% pranoprofen is applied 1–2 drops per dosage and 4 times per day. Total amount 75–100 mg per day of diclofenac sodium (voltaren) is divided into 3 portions, and is administered orally, while a suppository containing 25–50 mg of diclofenac sodium is administered 1–2 times per day.

EXAMPLES

The inhibition effect of argatroban on fibrin formation in the anterior chamber is explained by detailed Examples as follows. Those skilled in the art can understand that novel treatment methods of this invention provide decrease of fibrin formation after cataract operation, vitreous surgery, and glaucoma operation so as to result in more satisfactory restoration of visual acuity.

EXAMPLE 1

Fibrin Formation in the Anterior Chamber Caused by Laser Irradiation

Experimental Model

In this example, a model of fibrin formation in the rabbit anterior chamber caused by laser irradiation was used as a measure for testing the action of argatroban. In this model, the seriousness of inflammation and amount of fibrin are determined proportional to the total energy of the laser irradiation. The amount of fibrin can be controled to the desired value by altering total energy of laser irradiation. In this example, two conditions with smaller (condition A) and larger (conditionB) irradiation energy were used to test fibrin formation, finding that stronger fibrin formation was observed in the eyes treated with the larger total irradiation energy.

MATERIALS AND METHOD

Matured pigmented rabbits (Dutch rabbits of 2 kg body weight) were irradiated with laser at the iris using an argon laser equipment (product of NIDEK). In one group of the rabbits on the eyes, 8 irradiation points at the same interval on a circle line were made under the conditions of coagulation size of 50 micrometer, output of 1.0 Watt and irradiation time of 0.1 second (condition A). In another group of the rabbits, 8 irradiation points similar to those on the eyes were made under the conditions of coagulation size of 200 micrometer, output of 1.0 Watt and irradiation time of 0.2 second (condition B).

From 30 minutes prior to and until 30 minutes after irradiations, 0.1 mg/kg/minute of argatroban was administered intravenously from the ear vein. Control group received only laser irradiation. Positive control group received 1000 U/kg of heparin intravenously 30 minutes prior to laser irradiation.

For argatroban eye drop, right eyes of the rabbits received 5 mg/ml solution of argatroban, while left eyes were used as a control without application of argatroban.

The fibrin formation was recorded photographically using a slit lamp microscope.

Further, the laser irradiation of condition B was effected and then the anterior chamber flare values were estimated using the flare cell meter at 30 minutes and 60 minutes after the irradiation.

RESULTS

Figure 2:
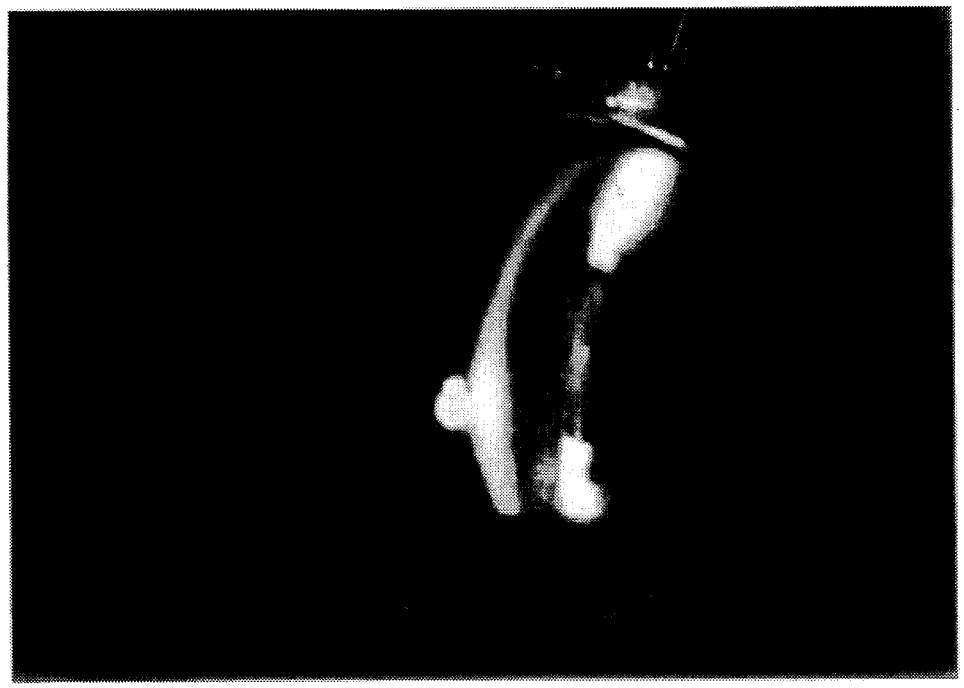
FIG. 2: Fibrin formation in the anterior chamber by the laser irradiation under condition B. This is a photograph replacing a figure showing the appearance of the animal.
Figure 3:
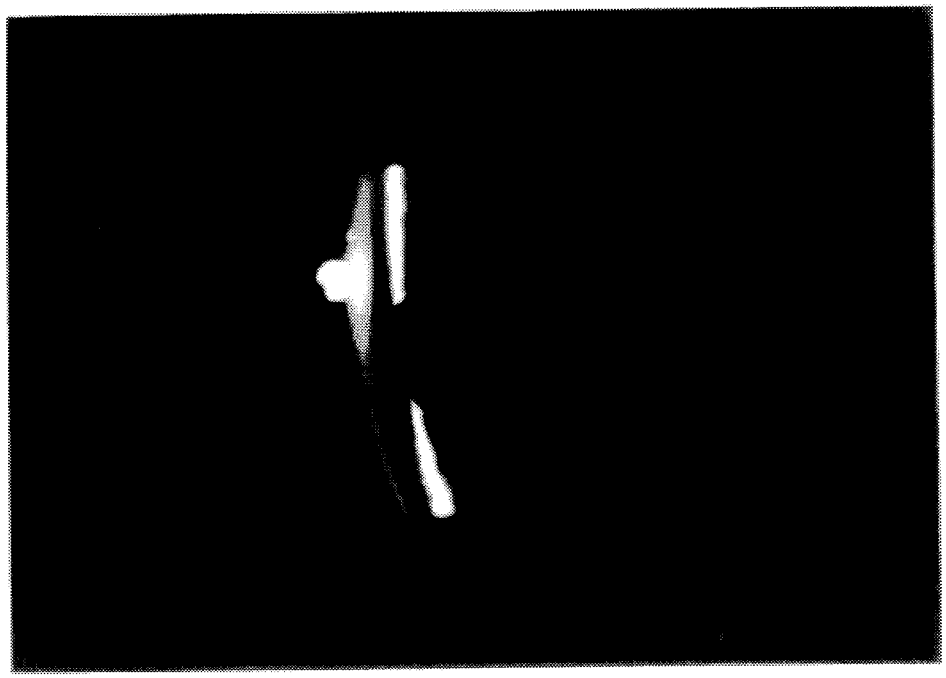
FIG. 3: Inhibition of fibrin formation caused by the laser irradiation under condition A in the anterior chamber with argatroban. This is a photograph replacing a figure showing the appearance of the animal.
Figure 4:
FIG. 4: Inhibition of fibrin formation caused by the laser irradiation under condition A in the anterior chamber with argatroban. This is a photograph replacing a figure showing the appearance of the animal.

In the control group, fibrin formation were observed in both of conditions A and B after 30 minutes. The results obtained by a slit lamp microscope for conditions A and B are shown in FIGS. 1 and 2, respectively. In the positive control group (heparin administered group), no fibrin formation was observed during 30 minutes to 3 hours observation time after the irradiation (The result is not shown). In the 0.1 mg/kg/minute argatroban administered group, no fibrin formation was also observed 30 minutes after the irradiation under both of conditions A and B, similar to the heparin administered group. The results under conditions A and B are shown in FIGS. 3 and 2 as attached.

The results of the flare cell meter observations are shown in Table 1 below.

The flare cell meter measures turbidity in the anterior chamber as the photon count. The following Table 1 shows that argatroban clearly inhibited the fibrin formation after 30 minutes and 60 minutes. This experiment also showed the inhibiting activity of argatroban against fibrin formation in the anterior chamber.

TABLE 1

The effect of argatroban on flare increase in the anterior chamber of pigmented rabbits after the irradiation of argon laser

| Medical | photon count (/msec) | | | |
|---|---|---|---|---|
| | 30 minutes after laser irradiation | | 60 minutes after laser irradiation | |
| control | 877.0 ± 333.8 | (n = 4) | 1002.9 ± 137.0 | (n = 4) |
| argatroban i.v. | 417.7 ± 159.3 | (n = 4) | 356.9 ± 168.3 | (n = 4) |
| argatroban eye drop | 287.7 ± 99.2 | (n = 4) | 341.2 ± 86.5 | (n = 4) |

Note: n = number of animals.
argatropan i.v. = intravenous injection at 0.1 mg/kg/min.
argatroban eye drop = a solution of 5 mg/ml concentration was used.

EXAMPLE 2

Fibrin Formation by Administering Self-Plasma to the Anterior Chamber

Experimental Model

Blood of matured white rabbits (2 kg in body weight) were taken and separated to give plasma. Two hundred microliters of anterior chamber liquid was taken by conducting centesis into anterior chamber of the same rabbit. Then, 150 microliter of the plasma obtained and 50 microliter of argatroban solution (10 mg/ml), 200 microliter in total, were injected to the anterior chamber from the same centesis portion. The control received 150 microliter of plasma and 50 microliter of physiological saline in the same manner at the anterior chamber. The fibrin formation in the anterior chamber 24 hours after the administration was observed and recorded.

RESULTS

Figure 5:
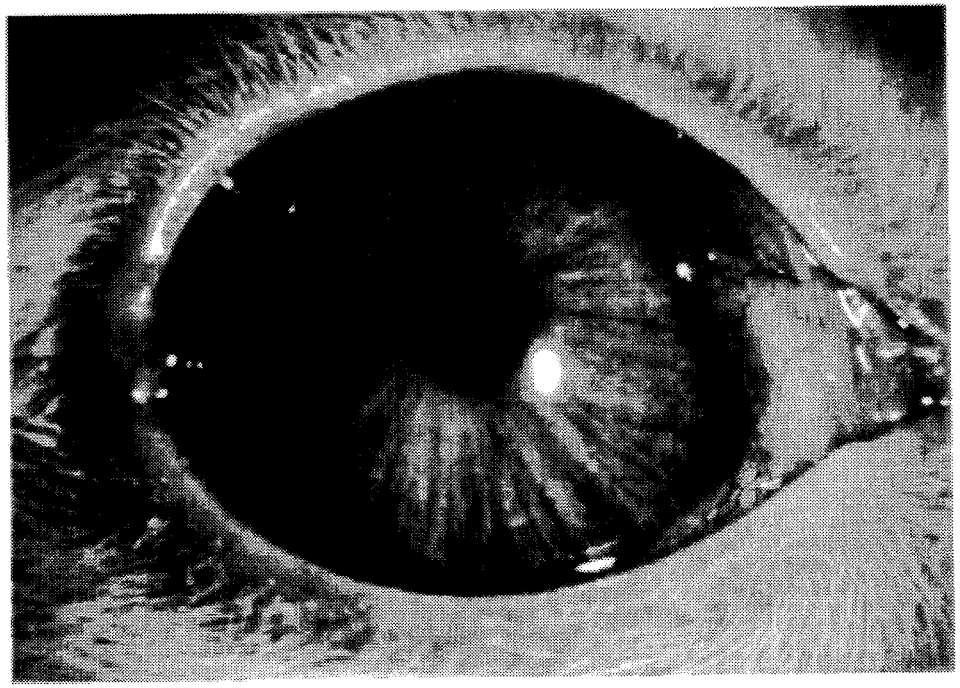
FIG. 5: Inhibition of fibrin formation caused by administering self-plasma in the anterior chamber with argatroban. This is a photograph replacing a figure showing the appearance of the animal.
Figure 6:
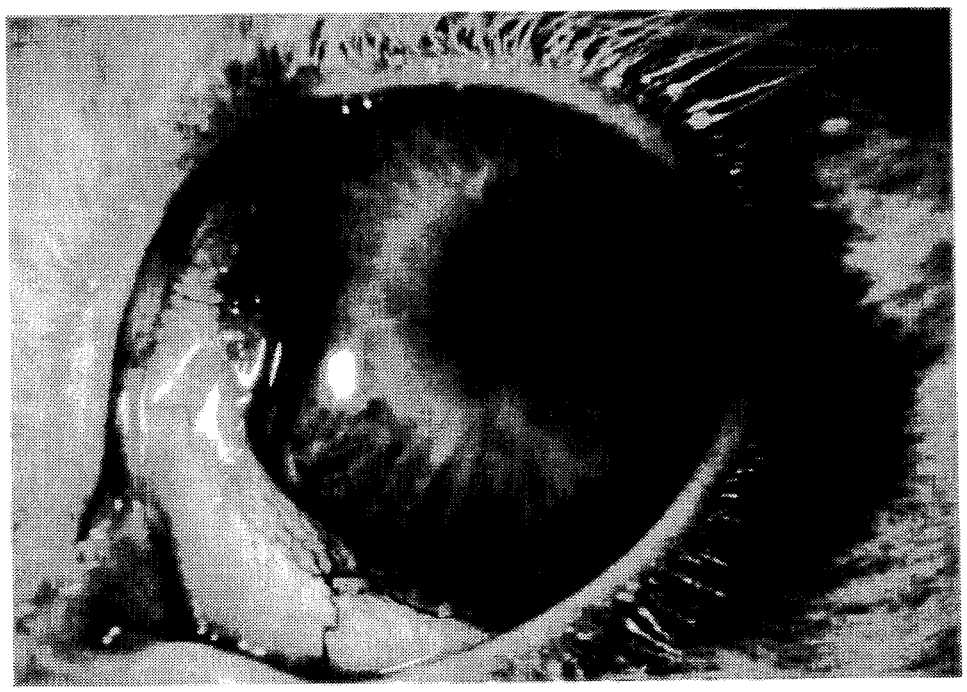
FIG. 6: Fibrin formation in the anterior chamber caused by administering self-plasma. This is a photograph replacing a figure showing the appearance of the animal.

No fibrin formation was observed 24 hours after the administration of arbatroban. On the contrary, a strong fibrin formation in the anterior chamber was observed in the control eyes. The obtained results are shown in FIGS. 5 and 6 as attached.

DISCUSSION

As is apparent from Examples 1 and 2 as described above, intravenous administration of argatroban provides complete inhibition of the fibrin formation in the anterior chamber in both of laser irradiation model and self-plasma injection model. This should be a result of competition of argatroban with the action of trombin during the course of conversion of fibrinogen to fibrin.

Argatroban will prevent the fibrin formation and blood clot formation by direct action on trombin, and it will not work on other coagulation systems. This means that less risk of bleeding after intraocular operation is expected as compared with other anticoagulating agents, e.g., heparin. If the argatroban administration ceases, the coagulating function of the body is recovered rapidly. It seems that argatroban is an extremely effective and safe drug for application in clinical ophthalmology.

In the following Table 2, the toxicological data of argatroban is shown.

TABLE 2

| | | LD50 of argatroban (mg/kg) | | | |
|---|---|---|---|---|---|
| animal | sex | i. v. | i. p. | subc. | p. o. |
| mouse | Male | >81 | 475 | 3750 | >15000 |
| | Female | >81 | 640 | 3900 | >15000 |
| rat | Male | >81 | 320 | 700 | >15000 |
| | Female | >81 | 409 | 620 | >15000 |
| dog | Male | >200 | — | — | — |
| | Female | >200 | — | — | — |

What is claimed is:

1. A method for inhibiting fibrin formation in the anterior chamber in mammals by prophylactically administering an effective amount of argatroban to mammals susceptible to said fibrin formation.

2. The method claimed in claim 1, wherein argatroban is administered directly into the anterior chamber.

3. The method claimed in claim 1, wherein administration of argatroban to the anterior chamber is conducted using a preparation of irrigating solution.

4. The method claimed in claim 1, wherein administration of argatroban to the anterior chamber is conducted using a preparation of eye drop.

5. The method claimed in claim 1, wherein administration of argatroban to the anterior chamber is conducted via intravenous administration.

6. The method claimed in claim 1, wherein administration of argatroban to the anterior chamber is conducted using a preparation of drip infusion.

7. A use of argatroban for inhibiting fibrin formation in the anterior chamber in mammals.

8. A process for inhibiting fibrin formation in the anterior chamber of a subject suspected to have destruction of BAB (Blood anterior chamber barrier), which comprises administering an effective amount of argatroban and an anti-inflammatory agent to such subject.

9. The process of claim 4 in which the fibrin formation is caused by severe and sudden damage.

10. The process of claim 9, in which the severe and sudden damage comprises surgery operation.

11. The process of claim 8, in which argatroban is administered by injection into intra-chamber, and the anti-inflammatory agent is administered by injection under conjunctiva.

12. The process of claim 8, in which the anti-inflammatory agent is asteroid agent.

13. The process of claim 8, in which the anti-inflammatory agent is a non-steroid agent.

14. The process of claim 8, in which antibacterial agent is further administered.

15. The process of claim 8 in which argatroban is administered in the form of an ocular perfusion.

16. The process of claim 8 in which argatroban is administered in the form of an eye drop.

17. The process of claim 8 in which argatroban is administered in the form of a drip infusion.

18. The process of claim 8 in which argatroban is administered in the form of an ointment.

* * * * *